United States Patent [19]

Yoshida et al.

[11] Patent Number: 5,723,976

[45] Date of Patent: Mar. 3, 1998

[54] METHOD FOR DETECTING MINUTE DEFECTS IN AN ENCAPSULATED ELECTRONIC COMPONENT

[75] Inventors: Toshiaki Yoshida, Ohtsu; Tetsuo Norimatsu, Shiga-ken, both of Japan

[73] Assignee: International Business Machines Corporation, Armonk, N.Y.

[21] Appl. No.: 529,387

[22] Filed: Sep. 18, 1995

[30] Foreign Application Priority Data

Sep. 22, 1994 [JP] Japan ................... 6-227865

[51] Int. Cl.⁶ ......................................... G01N 1/30
[52] U.S. Cl. ........................... 324/158.1; 250/302
[58] Field of Search ............... 73/36, 762, 865.8, 73/865.9, 866; 324/158.1; 250/302

[56] References Cited

U.S. PATENT DOCUMENTS

| | | | |
|---|---|---|---|
| 3,543,570 | 12/1970 | Mlot-Fijalkowski | 73/104 |
| 3,981,185 | 9/1976 | Molina | 73/104 |
| 4,400,618 | 8/1983 | Bupp et al. | 250/302 |
| 4,436,999 | 3/1984 | Kern | 250/302 |
| 4,909,806 | 3/1990 | Garbe | 8/647 |
| 5,030,701 | 7/1991 | Garbe | 526/245 |
| 5,369,983 | 12/1994 | Grenfell | 73/40 |

OTHER PUBLICATIONS

J. McCormick, Liquid Penetrant Testing For Microelectronic Package Hermeticity, Mar.–Apr. 1982, Institute of Electrical and Electronics Engineers, Inc. pp. 207–213.

Aaron Dermarderosian and Vincent Gionet, Water Vapor Penetration Rate into Enclosures with Known Air Leak Rates, Jan. 1979, vol. ED–26 No. 1, pp. 83–90.

W. Sander, Testing of components with perfluorinated liquids, Elektronik Journal, Apr. 1977, vol. 26, No. 4 pp. 93–94.

*Primary Examiner*—Ernest F. Karlsen
*Assistant Examiner*—Russell M. Kobert
*Attorney, Agent, or Firm*—Ira D. Blecker

[57] ABSTRACT

Minute defects in an encapsulated electronic component are detected by immersing the component in an aqueous solution of a water-soluble fluorescent substance having the property of fluorescing when moistened and stopping fluorescing when dry. The solution is allowed to permeate into minute defects of the component whereupon the component is opened. The defects are detected by observing an image of the component while moistening and drying the component to detect fluorescing and stopping fluorescing.

11 Claims, 1 Drawing Sheet

METHOD FOR DETECTING MINUTE DEFECTS IN AN ENCAPSULATED ELECTRONIC COMPONENT

FIELD OF THE INVENTION

The present invention relates to a method for detecting minute defects in an encapsulated electronic component, for example electronic components encapsulated with resins or ceramics. Such electronic components include, for example, integrated circuit chips containing resistors, microswitches or logic circuits, or electronic components used as contacts in relay circuits and the like.

BACKGROUND OF THE INVENTION

When materials such as resins and ceramics are used to encapsulate electronic components, it is required to detect the presence of minute defects on the surface of or inside such materials. In such a case, a method using an oil-based fluorescent solution has been used. In this method an electronic component such as an IC package is immersed in an oil-based fluorescent solution for a certain time to allow the oil-based fluorescent solution to permeate into minute defects, for example, locations where the resin is separated from the component, after which the encapsulating resin is opened and the electronic component is irradiated with ultraviolet rays to observe visually the fluorescing portions and their intensity to determine the adhesion of the encapsulation to the component.

However, if the encapsulating material is an organic substance such as a resin, the organic material itself often fluoresces by the irradiation of ultraviolet rays, and it is difficult to distinguish the fluorescence of the fluorescent solution which has permeated into minute defects. Also, to allow the oil-based fluorescent solution to permeate into minute defects the electronic component must be immersed in the solution overnight or even longer; thus the method cannot be used for urgent evaluation.

Furthermore, due to visual inspection using an ordinary ultraviolet irradiation device, the intensity of fluorescence is too small to evaluate minute portions of 100 microns or less. Also, since the fluorescent solution is oil-based, care must be taken for handling the solution for safety and for environment protection.

It is an object of the present invention to provide a method for detecting minute defects in electronic components in which these disadvantages are avoided or mitigated.

BRIEF SUMMARY OF THE INVENTION

The object of the invention has been achieved by providing a method for detecting minute defects in an encapsulated electronic component comprising the steps of immersing the component in an aqueous fluorescent solution of a water-soluble fluorescent substance having the property of fluorescing when moistened and stopping fluorescing when dry, allowing the solution to permeate into minute defects of the component, opening the component, and observing an image of the component while moistening and drying the component at least once to detect fluorescing and stopping fluorescing.

BRIEF DESCRIPTION OF THE DRAWINGS

Embodiments of the invention will now be described, by way of example, with reference to the accompanying drawings, wherein.

DETAILED DESCRIPTION OF THE INVENTION

A component to be tested is immersed in an aqueous fluorescent solution. The aqueous fluorescent solution contains a water-soluble fluorescent compound which fluoresces when moistened and stops fluorescing when dried. The water-soluble fluorescent compound may be an organic fluorescent compound having a benzene, pyridine, γpyrroline, pyrazine, oxazine or thiazine ring.

Figure 1:
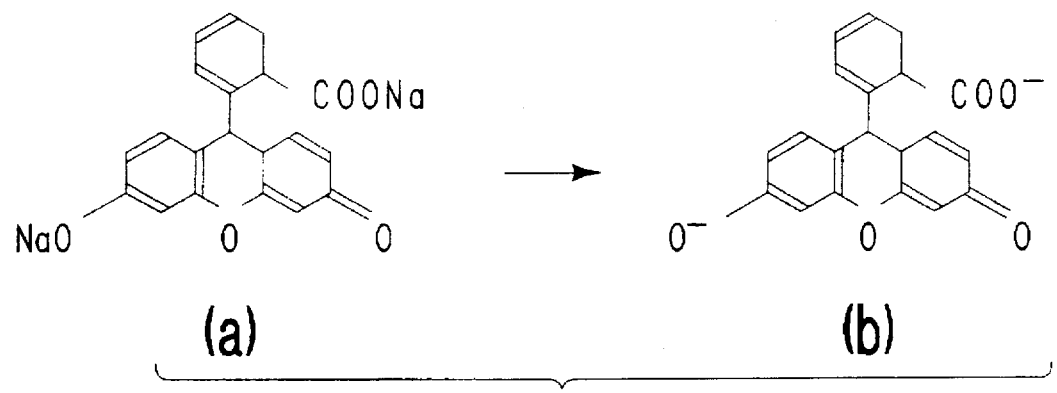
FIGS. 1 and 2 show the chemical formulae of fluorescent substances which may be used in performing the invention.

For example, fluorescein sodium (uranine) is a reddish orange-coloured crystalline compound whose chemical formula is shown in FIG. 1. This does not fluoresce when it is dry (FIG. 1a) but emits yellowish green fluorescence when it is dissolved in water (FIG. 1b).

Figure 2:
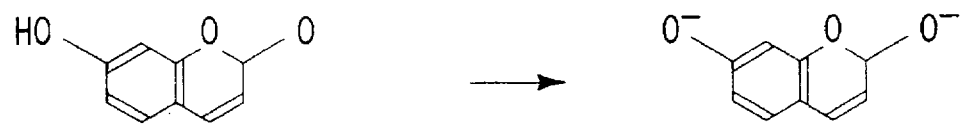

Likewise, Umbelliferone (FIG. 2) is a colourless crystalline compound which does not fluoresce when it is dry (FIG. 2a) but emits blue fluorescence when it is dissolved in water (FIG. 2b).

Thus, fluorescein sodium emits yellowish green fluorescence when moistened and stops fluorescing when dried, while umbelliferone emits blue fluorescence when moistened and stops fluorescing when dried. Since fluorescein sodium is easily dissolved in cold water, and is stable and difficult to decompose, it is especially suitable for the use in the aqueous fluorescent solution of the present invention.

Theoretically, the water-soluble fluorescent compound can be used in concentrations from trace (0.0001% by weight in the solution) to saturation. However, if the concentration of the water-soluble fluorescent compound in the aqueous fluorescent solution is too low, the intensity of fluorescence requires a long time for detection, while above a certain concentration the time for detection is not reduced. Considering economy, therefore, the concentration of the water-soluble fluorescent compound in the solution is 0.0001 to 3% by weight, preferably about 1% by weight. For the detection of a minute gap in the component to be tested, such as a gap of a width of about 0.1 micron, a concentration of about 1% by weight is sufficient.

It is preferred that the aqueous fluorescent solution comprises a water-soluble fluorescent compound, a surface active agent and a solvent. Although pure water is preferable as the solvent, organic solvents may be used for this purpose. When organic solvents are used, such solvents should not affect the water-soluble fluorescent compound and the encapsulating resin for electronic components. For this reason, alcohols such as ethyl alcohol are preferred.

By mixing a surface active agent to the aqueous fluorescent solution, the surface tension of the solution is lowered, and the solution permeates more easily into minute defective portions of the component to be tested when the component is immersed in the solution.

Any anionic, cationic, amphoteric or nonionic surface active agent may be used for this purpose. Anionic surface active agents include carboxylates, sulphonates, sulfuric esters, and phosphoric esters; and cationic surface active agents include amine salts, quaternary ammonium salts, phosphonium salts, and sulfonium salts. Amphoteric surface active agents include betaine and sulfobetaine; and nonionic surface active agents include aliphatic monoglycerine esters, aliphatic polyglycol esters, aliphatic sorbitan esters, and polyethylene glycol type surface active agents.

The surface active agent may be used in any concentration higher than the critical micell concentration. For example, the critical micell concentration of an anionic surface active agent, sodium alkylbenzene sulphonate (ABS), is about 0.0001% by weight.

An anionic surface active agent, especially sodium alkylbenzene sulphonate (ABS), is advantageously used in the method of the present invention because it is stable, difficult to decompose, inexpensive, and does not affect organic materials such as encapsulating resins.

The component to be tested is immersed in the aqueous fluorescent solution comprising the water-soluble fluorescent compound, surface active agent and solvent. The conditions for immersing differ depending on the shape, size and material of the component, and the object of the evaluation. It may be desirable to accelerate the permeation of the solution into the component, and if so it is not always required to add a surface active agent to the aqueous fluorescent solution.

When the accelerating operation is performed, the immersion time may be reduced significantly. The operation for accelerating the permeation of the aqueous fluorescent solution may include (1) boiling the aqueous fluorescent solution when the component is immersed in the solution, (2) immersing the component in the solution under a reduced pressure, or (3) immersing the component in the solution at a high temperature and under a high pressure.

For example, when the solution is boiled, it is preferred to boil the solution under normal pressure for about 30 minutes; when a reduced pressure is used, it is preferred to perform the operation at room temperature at a pressure of 23 hPa or below for about 30 minutes; and when a high temperature and high pressure are used, it is preferred to perform the operation, for example, in an autoclave at a pressure of about 1500 hPa at a temperature of about 112° C. or above for about 10 minutes. In the last case, the temperature should be the same as the test temperature for the component to be tested, such as a semiconductor device, but may be elevated up to about 200° C. The time for immersion must be decided depending on the particular component under test, since if the immersion time is unnecessarily prolonged an excessive amount of the fluorescent solution permeates into the component and it can be difficult to determine precisely where the defects are located.

When an accelerating operation is performed at a high temperature it is preferred to use sodium alkylbenzene sulphonate (ABS) as the surface active agent, which is an anionic surface active agent with a high heat resistance and has a large effect even in a small amount. To further improve detection, the component to be tested may be immersed in an ultrasonic cleaner for 1–2 minutes prior to the immersion of the component in the aqueous fluorescent solution. Although the use of pure water as the solvent has been described, the viscosity of the aqueous fluorescent solution is not especially important if only cracks in the component are to be detected, and alcohols such as ethyl alcohol may be used as the solvent instead of pure water.

After immersing the component to be tested in the aqueous fluorescent solution to allow the solution to permeate into minute defects of the component, the component is opened. This may be done using a vice with a cutter for opening packages, or using cutting pliers or a grinder. Other means for opening may be used, provided it is a dry system without using water or oil.

After opening the component it is moistened and dried at least once. An example of an apparatus for moistening and drying the component is shown in FIG. 3.

Figure 3:
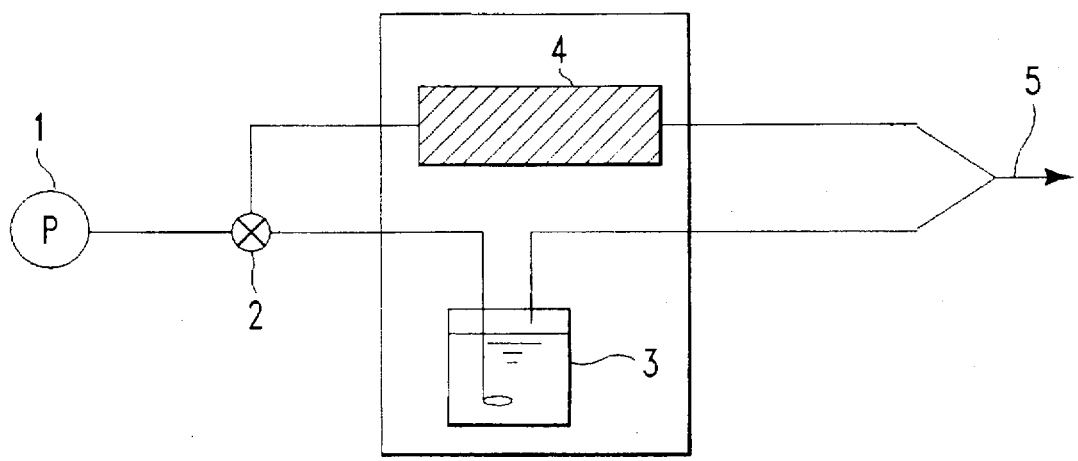
FIG. 3 is a schematic diagram illustrating an example of a humidifying and dehumidifying apparatus which may be used in performing the invention.

In the apparatus shown in FIG. 3, air is supplied from an air pump 1, and the path of the air may be switched by a change-over valve 2 either through a humidifier 3 or through a dehumidifier 4. Dry air or humid air is blown out of a nozzle 5 according to the setting of the valve 2. The humidifier 3 generates humid air from a constant temperature vessel at a temperature from room temperature to 60° C. by the use of bubbling or ultrasonic waves, and the dehumidifier 4 is filled with a drying agent such as silica gel.

The opened component to be tested is fixed on a sample table installed near the nozzle 5. The component to be tested is repeatedly moistened and dried with this apparatus. The component should be moistened such that the fluorescent solution permeating into the component does not diffuse into the water drops produced by moistening. To achieve this, the component is normally moistened for about 2 minutes and thereafter dried for about 10 minutes for complete drying.

Although the step of moistening and drying may be performed once if fluorescing and stopping fluorescing caused by the single step can be adequately seen, it is preferred to perform the step repeatedly.

An enlarged image of the component is observed while moistening and drying the component to detect the location and degree of minute defects of the component. The observation may be carried out, for example, by irradiating the component with ultraviolet rays and observing the defect through a fluorescent microscope, or by inspecting the fluorescence using image processing.

Example 1

An aqueous fluorescent solution consisting of

| Fluorescein sodium | 1 part by weight |
| Sodium alkylbenzene sulphonate | 1 part by weight |
| Pure water | 98 parts by weight | and a 4M-DRAM (20-pin SOJ) manufactured by IBM Japan were used for the test. The component was immersed in the fluorescent solution in an autoclave at 112° C. under about 1530 hPa (about 1.56 kgf/cm$^2$) for 10 minutes.

After the encapsulating resin of the above electronic component (o-cresol novolak resin) was opened using a vice with a cutter, the opened electronic component was placed near the nozzle 5 shown in FIG. 1, subjected to cycles of 2 minutes of moistening and 10 minutes of drying, and the state of fluorescing and stopping fluorescing was observed using a fluorescence microscope (Olympus). The result showed that the location of fluorescing (the location in which the fluorescent solution permeated) was the side of the lead pin, and that the location extended in a width of about 0.1 micron to the wire connecting the chip with the lead pin in the package.

Example 2

An aqueous fluorescent solution consisting of

| Fluorescein sodium | 1 part by weight |
| Polyoxyethylene glycol | 1 part by weight |
| Pure water | 98 parts by weight | and a microresistor (8-pin SOP) manufactured by Omron were used for the test. The component was immersed in the fluorescent solution at room temperature under normal pressure for 24 hours.

After the encapsulating resin of the above electronic component (o-cresol novolak resin) was opened using a vice with a cutter, the opened electronic component was placed near the nozzle shown in FIG. 1, subjected to cycles of 2 minutes of moistening and 10 minutes of drying, and the state of fluorescing and stopping fluorescing was observed using a fluorescence microscope (Olympus). The result showed that the location of fluorescing (the location in which the fluorescent solution permeated) was the entire surface of the lead pin, and that the location extended in a width of about 1 mm to the organic resistor in the package.

It will be apparent to those skilled in the art having regard to this disclosure that other modifications of this invention beyond those embodiments specifically described here may be made without departing from the spirit of the invention. Accordingly, such modifications are considered within the scope of the invention as limited solely by the appended claims.

We claim:

1. A method for detecting minute defects in an encapsulated electronic component comprising the steps of immersing the component in an aqueous fluorescent solution of a water-soluble fluorescent substance having the property of fluorescing when moistened and stopping fluorescing when dry, allowing the solution to permeate into minute defects of the component, opening the component, and observing an image of the component while moistening the component with humid air and drying the component with dry air at least once to detect fluorescing and stopping fluorescing.

2. The method as claimed in claim 1 wherein the aqueous fluorescent solution comprises a water-soluble fluorescent substance, a surface active agent and a solvent.

3. The method as claimed in claim 2 wherein the water-soluble fluorescent substance is an organic fluorescent compound having a benzene, pyridine, α-pyrroline, pyrazine, oxazine or thiazine ring.

4. The method as claimed in claim 2 wherein the surface active agent is an anionic surface active agent.

5. The method as claimed in claim 2 wherein the water-soluble fluorescent substance is present in an amount from 0.0001% by weight to saturated concentration.

6. The method as claimed in claim 2 wherein the water-soluble fluorescent substance is present in an amount from 0.0001 to 3% by weight.

7. The method as claimed in claim 2 wherein the water-soluble fluorescent substance is present in an amount of about 1% by weight.

8. The method as claimed in claim 1 wherein the step of allowing the solution to permeate into minute defects of the component further includes accelerating the permeation of the solution into the component.

9. The method as claimed in claim 8, wherein accelerating the permeation of the solution into the component includes boiling the aqueous fluorescent solution when the component is immersed therein.

10. The method as claimed in claim 8, wherein accelerating the permeation of the solution into the component includes applying a reduced pressure to the fluorescent solution when the component is immersed in the fluorescent solution.

11. The method as claimed in claim 8, wherein accelerating the permeation of the solution into the component includes applying a high temperature and high pressure to the fluorescent solution when the component is immersed in the fluorescent solution.

* * * * *